United States Patent [19]
Truett

[11] Patent Number: 5,453,252
[45] Date of Patent: Sep. 26, 1995

[54] SCREEN CELL FOR SPECTROSCOPY

[76] Inventor: William L. Truett, HCR #33, Townshend, Vt. 05353-7702

[21] Appl. No.: 201,797
[22] Filed: Feb. 25, 1994
[51] Int. Cl.$^6$ ....................................................... B01L 9/00
[52] U.S. Cl. .......................... 422/104; 422/102; 356/244; 356/246; 446/16
[58] Field of Search .............................. 436/164; 422/57, 422/102, 104; 356/244, 246; 446/15, 21, 16; D21/61; 250/459.1, 458.1

[56] References Cited

U.S. PATENT DOCUMENTS

| | | | |
|---|---|---|---|
| 3,515,490 | 6/1970 | Dreyfus et al. | 356/244 |
| 5,093,160 | 3/1992 | Johnson et al. | 427/358 |
| 5,095,213 | 3/1992 | Strongin | 250/459.1 |
| 5,182,191 | 1/1993 | Fan et al. | 435/7.9 |
| 5,217,619 | 6/1993 | Redmond, Jr. et al. | 210/650 |
| 5,290,705 | 3/1994 | Davis | 436/164 |

OTHER PUBLICATIONS

"3M" Literature—3 items.
N. L. Owen & S. G. Wood, Infrared Analysis, Using Tissue Paper, Journal of Chemical Education, 64, 977 (1981).
E. D. Black et al., Sample Handling for Qualitative IR Microspectrocopy, Anal. Chem., 29, 169 (1957).

*Primary Examiner*—David A. Redding
*Attorney, Agent, or Firm*—Herbert M. Wolfson

[57] ABSTRACT

A specimen support for optical observation or analysis is disclosed. The support comprises a disc-like member composed of a rigid material and having a plurality of holes extending therethrough, preferably in a screen of substantially equal-sized holes. When analyzing a liquid specimen, the disc is dipped in the liquid and the surface tension of the liquid will cause the liquid to bridge or span the holes. The support is then placed vertically in a tray or holder and exposed to an infrared beam that passes horizontally through the holes to generate an infrared spectrum.

2 Claims, 4 Drawing Sheets

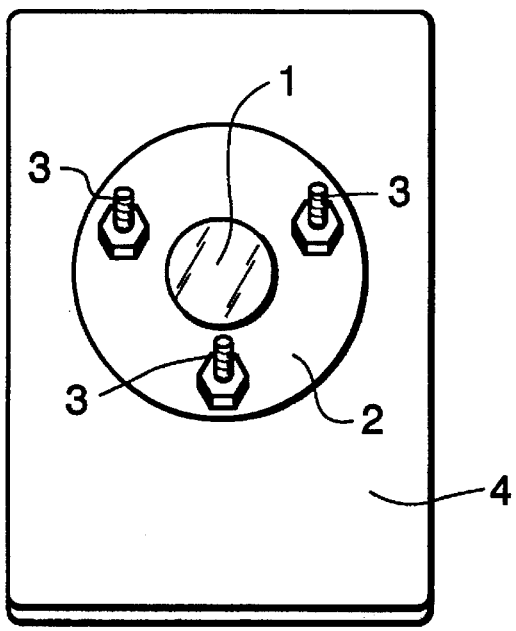
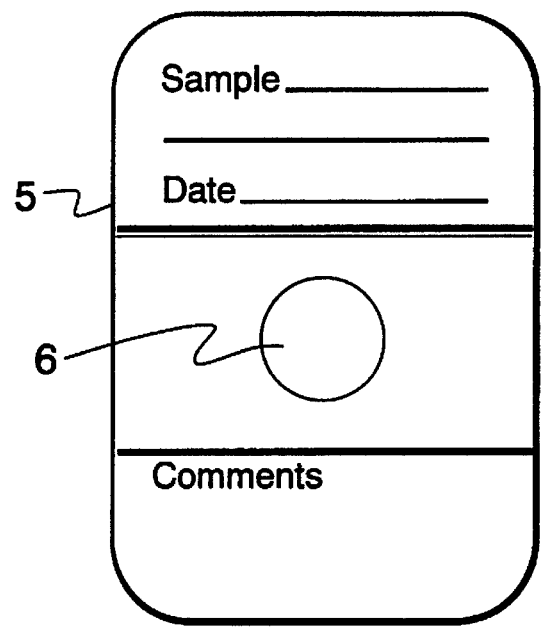
FIG. 1 PRIOR ART
Fig. 2 PRIOR ART
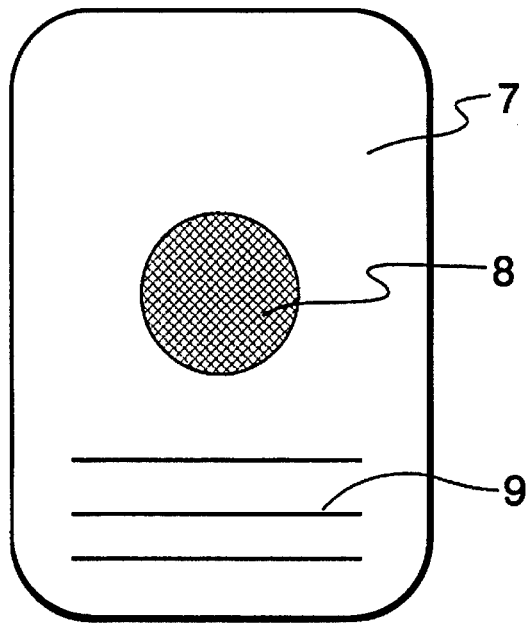
Fig. 3

Fig. 4
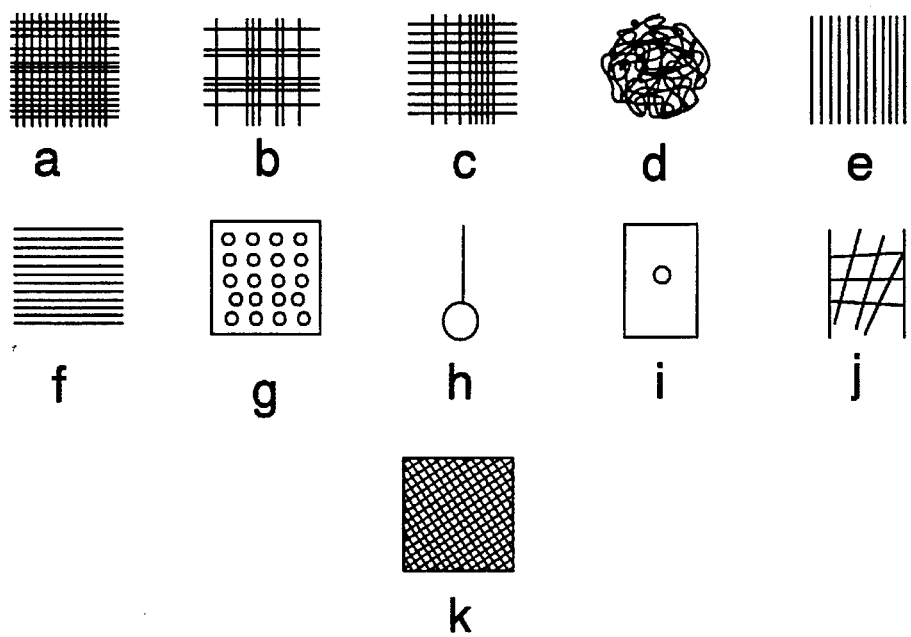
a  b  c  d  e
f  g  h  i  j
k
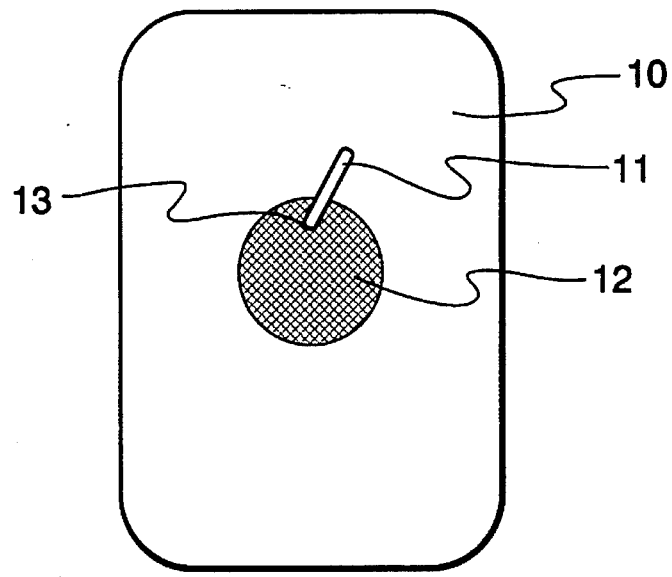
Fig. 5

SCREEN CELL FOR SPECTROSCOPY

BACKGROUND OF THE INVENTION

1. Field of the Invention

This invention is concerned with placing a liquid, a past, powder or a solid sample on a screen in order that a spectrum can be determined in a spectrometer, with the screen being fixed to a holder which will permit the screen being placed in the energy beam of the spectrometer.

2. Description of the Prior Art

The art of placing samples in spectrometers is a very old one and was well developed prior to 1940. Although developments in placing samples is spectrometers in order that their spectra may be determined is very well established in infrared spectrometers, and in particular in Fourier Transform Infrared (FTIR) Spectrometers, parallel developments have also taken place in UV spectrometers, visible light spectrometers, near infrared spectrometers, far infrared spectrometers, Raman spectrometers and fluorescence spectrometers to achieve the same ends. The attention will largely be concentrated on the FTIR spectrometer.

In order to determine qualitative spectra of liquids, solids and pastes, several methods have been developed. FIG. 1 shows a device known as a demountable cell. Two suitable windows of IR transmitting material, such as sodium chloride 1 are held in place by a retaining ring 2 which is held in position three bolts and nuts on a mounting plate 4 which fits into the cell slide of all commercial FFIR spectrometers. The cell slide insures that the sample held between the windows 1 will be in the energy beam of the spectrometer. The remountable cell, FIG. 1 is loaded by placing one or two drops of liquid between the windows 1 and placing the windows 1 on the plate 4 attaching the retainer ring 2 to upright bolts 3 and placing a nut on each bolt 3 and tightening down to the desired level. The cell is simple to assemble and disassemble, but the sodium chloride windows are expensive, subject to attack by moisture and many solvents, and is fragile. The use of the demountable cell applies to liquids or pastes but not to solids.

FIG. 2 depicts a card 5 containing a porous polyethylene or porous polytetrafluoroethylene window 6 upon which a sample of liquid or solution of a solid, or a paste can be placed. The card, FIG. 2, is then placed in the cell slide of an FTIR spectrometer and a spectrum determined. The problem with this device is that the spectrum of the porous paper is also determined in addition to that of the sample applied to the card window. This complicates the interpretation of the IR spectrum and renders information in four critical areas of the spectrum uncertain in the case of the polyethylene window, and several valuable areas am also useless when the polytetrafluoroethylene paper is used.

Thus, no simple means is presently available in commerce to obtain an FTIR spectrum of a liquid, paste or solid sample untrammeled by an additional spectrum.

SUMMARY OF THE INVENTION

The present invention is a method of applying a liquid, solid, paste or powder to a screen in such a fashion that the screen retains a thin layer of the sample. When the screen is placed in the sample compartment of the IR Spectrometer, a spectrum is easily obtained. The advantages of such a cell are considerable. First, the device is simple to use and if desired cleaning is quite easy, second, it can be used in any wavelength range of the electromagnetic spectrum from the vacuum UV to the far IR, third, no corrosion or wear as well as no fragility, fourth, the screen cells are very modest in cost, can easily be reused in many cases and can be discarded with no hazard to the environment.

In addition to the application of the screen cell to liquids or solutions, it can also be used for pastes or powders which can be smeared onto the screen. The same advantages apply that apply to the use of the cell with liquids.

The application of the screen cell to determining the spectra of solids can be achieved in several ways. In the first way, the solid is dissolved in a suitable volatile liquid which is then applied to the screen and upon evaporation, leaves a thin layer. The screen is then inserted in a suitable spectrometer, as a Fourier Transformer IR spectrometer, and a spectrum determined. Alternately, one can place the screen cell on a flat metal surface, apply the powdered solid to the screen, add a second piece of flat metal, place the metal screen - metal sandwich in a high pressure press and generate a clear fiber of the solid. Such films tend to be thicker than those generated by the afore noted solvent deposition.

The advantages to this technique are the same as the first three under "liquids" above, but the screen can not be reused although the cost is still modest and discard is a minor problem. Unlike the screen cell used with liquids, the screen cell used with solids can be stored very nicely and permanent collections maintained.

Although the technique of the screen cell works well with FTIR spectrometers, it is by no means limited to the technique and will find application in the following types of spectrometers: vacuum UV, UV, Visible light, NIR, FIR, Raman and fluorescence.

The application of pastes to the screen cell is very simple, a small spatulas being used to spread the material into a transmissive layer. The application of a thin film of powder can be done in a similar fashion, the powder being spread on the screen cell into a thin transmissive layer.

In addition to ease of measurement by transmission in spectrometers, it is also simple to measure samples which can be applied to screen cells by various means in various reflection modes. Samples can be examined by diffuse reflection and/or specular reflection when the necessary accessories are available for the various spectrometers.

An additional use of the screen cells, particularly when the scrim type of screen cell is in use, is to place a reagent or reagents on the screen which will react with a sample applied to the screen. In this fashion blood or urinalysis can be carried out and the analytical results determined on the appropriate spectrometer.

The screen type of cell and scrim type of screen cell in particular can be used to advantage with FTIR microscopes, permitting, for example, examination of many small samples, and biological samples in particular.

A critical property of the screen cell is that the cell transmit sufficient energy in order to determine a spectrum with the desired spectrometer. A second critical property of the screen cell is that it has no absorption spectrum when placed in the spectrometer. All screen cells meet these two essential criteria.

BRIEF DESCRIPTION OF THE DRAWINGS

FIG. 1 is a front view of a demountable cell holding two windows.

FIG. 2 is a front view of a cardboard holder or a polyethylene paper cell.

FIG. 3 is a front view of a screen cell.

FIG. 4 is a series of front views of various screen types.

FIG. 5 front view peg holder on plate for screen.

DETAILED DESCRIPTION OF THE PREFERRED EMBODIMENT

Figure 6:
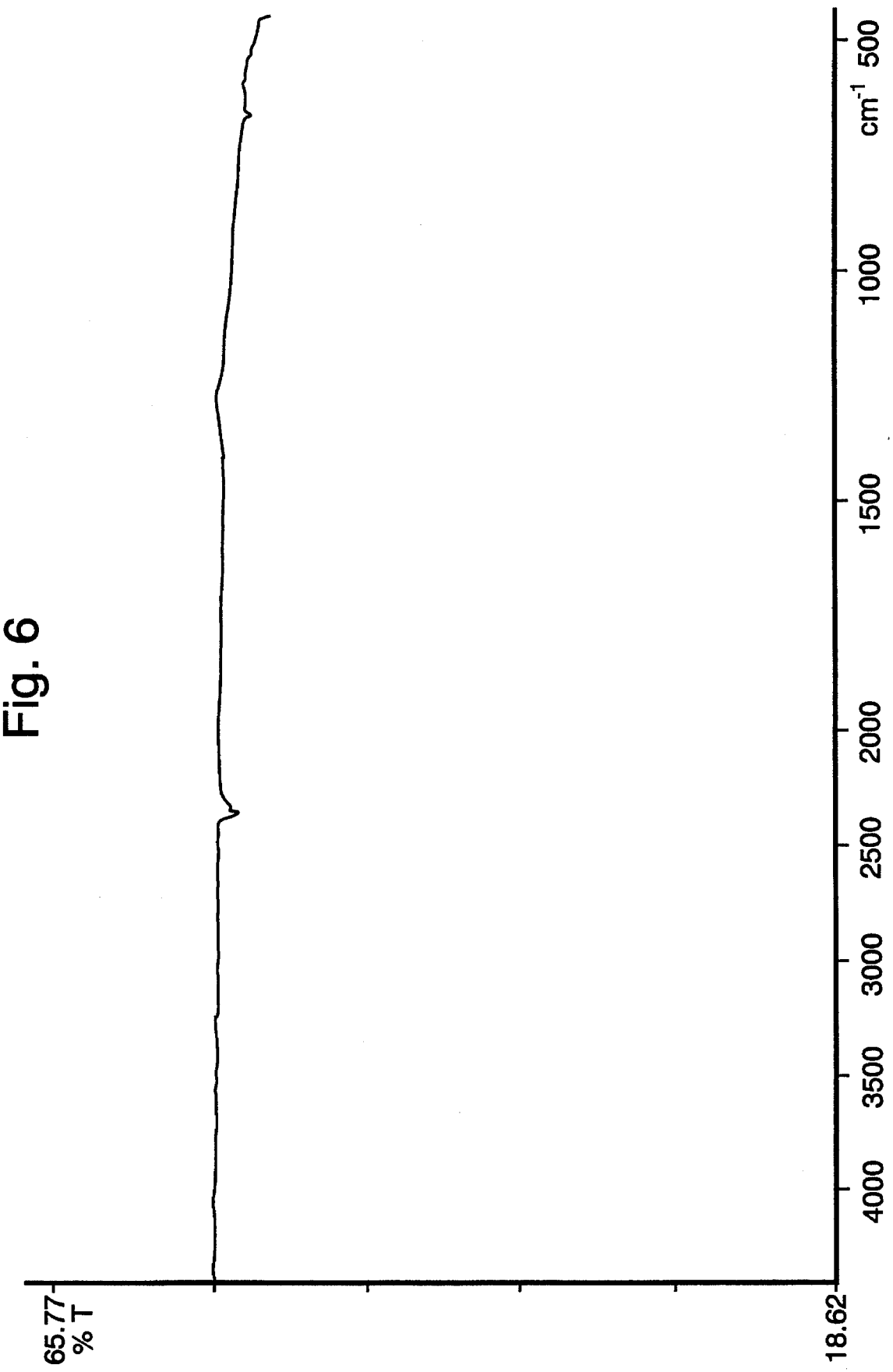
FIG. 6 background spectrum of screen cell.

The screen cell, FIG. 3, consisting of a holder 7 to which a screen 8 is attached by a suitable means such as adhesives, adhesive tape, Velcro™, and an identifying legend 9 which is positioned in the cell slide of any desired spectrometer.

The purpose of the screen cell shown in FIG. 3 is to facilitate the rapid qualitative spectrum of liquids, pastes, powders, and solids. The infrared spectrometer, precisely the Fourier Transform IR Spectrometer will be used to illustrate the technique, but the screen cell is broadly applicable to all types of spectrometers, including but not limited to the following: Vacuum UV, UV, Visible light, Near Infrared (NIR), Infrared, Far Infrared (FIR), Fluorescence and Raman. In each case, the holder geometry can be easily adapted to the sample holder of the spectrometer in use. In the case of the IR spectrometers, all of the IR instruments have uniform dimension cell slides which will accept holders.

The precise nature of the screen can vary dependent upon the usage. Basically, the screen types which can be employed in the screen cell are shown in FIG. 4. FIG. 4a is the classical screen grid normally seen in window screens and is uniform with regard to the apertures at 1.0 mm±10%. In addition to the uniform screen, non-uniform screens are also manufactured FIG. 4b as well as non-uniform screens with graded change in aperture. FIG. 4c, an additional applicable type for use in screen cells is a chaotic mesh of the sort that would be realized from the use of glass wool. FIG. 4d, although the grid type of screen is the preferred type, the parallel types shown in FIG. 4e and FIG. 4f are also applicable for use in the screen cell. It is also possible to use screen like materials such as the perforated plates shown in FIG. 4g. The simple loop, FIG. 4h may also be employed, as well as the simple aperture FIG. 4i. Two other types are of interest, FIG. 4j which is a screen with random apertures, and FIG. 4k is screen commonly known as a scrim which is usually a tight network of fibrous materials. The latter case of FIG. 4k has the appearance of a thin sheet of paper; however, sufficient energy to determine a spectrum is passed by this type of screen, and it does not possess a spectrum in the infrared. With regard to the materials of construction for the screens, a very wide range of materials can be utilized. The most common screens are from glass fibers with a coating of polymers, usually poly (vinyl chloride), but screens from quartz fibers are also available, as well as screens fashioned from various metals and metal alloys, including the noble metals. Ceramic materials can be fabricated into screens, as can a very wide variety of plastic and elastomeric materials, such as nylons, polyethylene, polystyrenes, fluoropolymers such as polytetrafluoroethylene, polyamides, polyphenylene sulfide, PEEK, polybutadiene and silicone polymers. The use of textile fibers both synthetic and natural can be considered for special purposes, very likely one-time uses, as in the application of screen cells to medical analysis.

FIG. 5 Peg holder for screen cell is an alternate to FIG. 3 screen cell with screen attached by adhesive. FIG. 5 shows a peg holder 11 mounted on cardboard or plastic plate 10 with a screen 12 attached by means of the peg fitted into a hole 13 in the screen.

Figure 7:
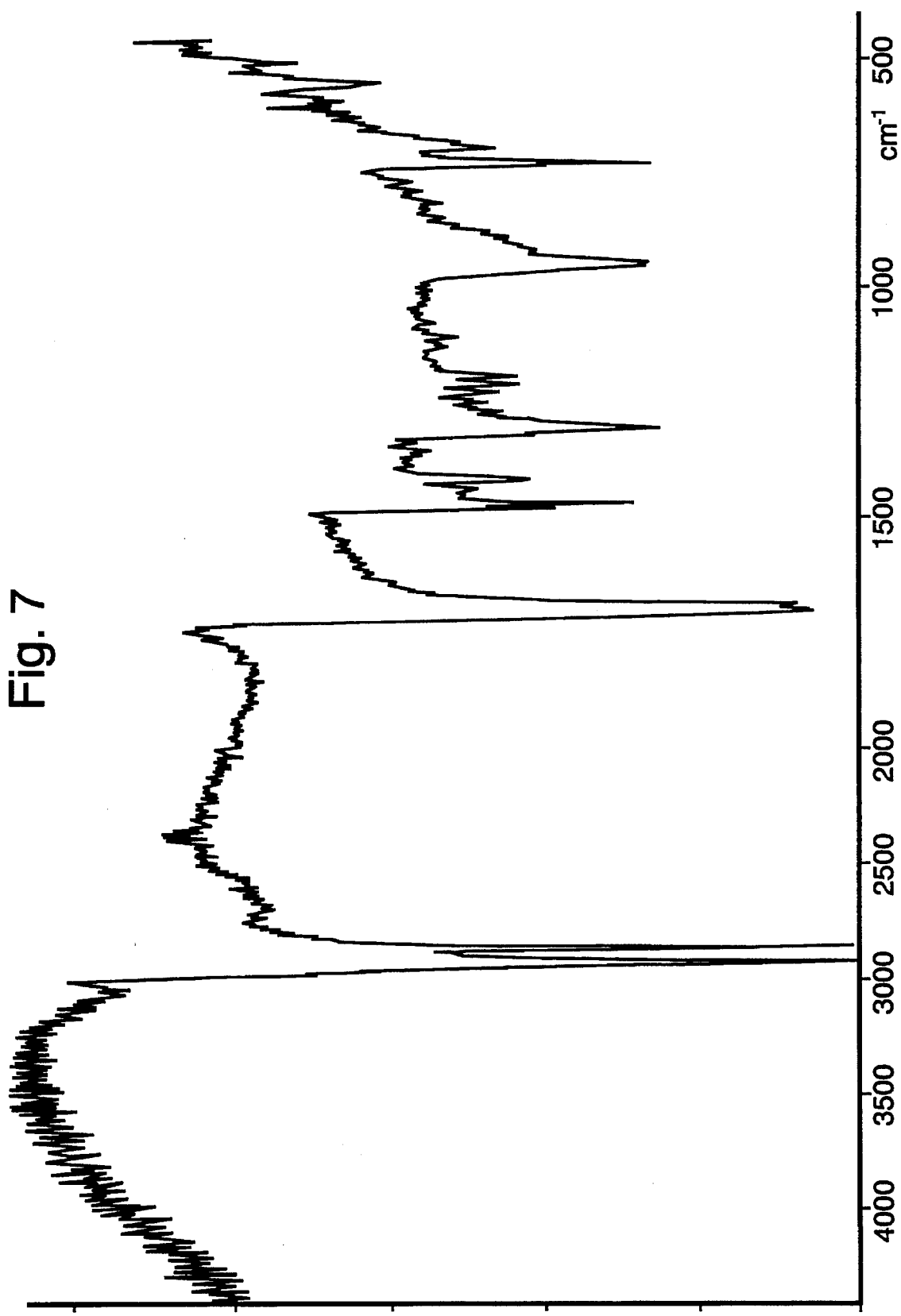
FIG. 7 spectrum of stearic acid on screen cell.

FIG. 6 is the background spectrum of the screen cell which clearly indicates that the screen cell has no infrared absorbance in the range of 4,000 to 500 cm$^{-1}$. FIG. 7 is an example spectrum of stearic acid using the screen cell in a spectrometer.

The material of construction of the holder for the screen portion of the screen cell are many. The paper or cardboard holder will be the most common, but the mode of affixing the screen to the holder need not be solely the adhesive type; the screen can also be affixed to the holders by placing a Velcro™ strip on the holder and screen, or via using a strip of durable stick tape on the face of the holder, or by placing one or more hooks on the holder, which engage perforations in the screen. The holder materials can be: paper, cardboard, plastic, metal, metal alloys, glass, ceramic and elastomers.

Loading of the screen cell when used for determining the spectra of liquids or solutions is simple. A Pasteur pipette is touched to the upper edge of the screen, holding the screen cell in a vertical position, and 0.2 ml is applied. The tip of the pipette can be used in order to spread the liquid out into a uniform layer such that at least all the screen apertures in the center portion of the screen are covered with liquid. The screen cell is then promptly placed in the cell slide of the IR spectrometer and a rapid scan determined, usually requiring 1–4 seconds. The need for speed relates to the fact that the spectrum must be determined before evaporation can take place. This time constraint is true, of course, with volatile liquids only, samples of viscous liquids, pastes, powders and solids can be determined at convenience.

The loading of a paste, or viscous sample to a screen cell is accomplished by placing a small aliquot of paste on the screen and the use of a small spatular to make a thin even layer. The spectrum is then determined promptly before the sample dries, and the thickness adjusted with the spatula if necessary.

The nature of the type of material of construction of the screen will vary with the liquid or paste being applied as well the material of construction of the holder. For non-viscous liquids such as acetone, the usual glass fiber-polymer coated screen is adequate with paper or cardboard holder. When corrosive but non-volatile materials are used, the glass fibers polymer coated screens are adequate, but in addition to the cardboard holder, it will be desirable to position a layer of inert absorbent in the holder. With phosphoric acid, this use of absorbent would be satisfactory, but not with strong oxidizing agents such as concentrated sulfuric acid, concentrated nitric acid, concentrated potassium hydroxide, or concentrated hydrogen peroxide. Strong reducing agents such as hydrazine should also be avoided. MSDS materials safety data sheets should be consulted when in doubt.

The determination of the spectra of solids using the screen cell technology can be achieved in two ways. In the first way, the solid is placed in solution in a suitable solvent via preparing a twenty to thirty percent solution of the solvent by warming the solvent solid mixture. It is desirable to prepare a concentrated solution in order that evaporation on the screen will rapidly yield a thin layer of solid. This is accomplished by applying about 0.2 ml of the saturated solution to the upper edge of the screen, which is held in a vertical position. The thickness of the cast film should, in general, be kept to a minimum; however, when spectra are being determined utilizing an NIR spectrometer a thick layer will be desirable since NIR bands show lower absorbance than IR bands. Thus, the sample thickness must be tailored to the spectroscopy technique employed. If the solid can not be readily placed in solution, a spectrum can be determined via pressing a sample of solid into the screen using a high pressure press. A simple sandwich is formed from a flat metal plate, 2×2", a 1" diameter circle of screen, the screen lightly coated with powdered solid, a second flat metal plate, 2×2" and the resultant sandwich place in a press at a pressure of 5 to 10 tons.

When removed from the press the screen upon examination will be covered with a film of solid. This filled screen can be placed in a simple paper folder, glued into place, inserted in the cell slide of an IR spectrometer and a spectrum determined depending upon the spectroscopy technique utilized, the desired thickness of the film will show considerable variation, but for FTIR spectroscopy a very thin film will be desired.

The use of multiple screens is a modification of the single screen cell which has the advantage that a greater thickness of sample can be realized which would be convenient with techniques such as NIR spectroscopy that requires a thick sample, an additional advantage of multiple screens is that the sample of liquid is less likely to evaporate.

Application of the screen cell is not limited to the determination of transmission type spectra, liquids, pastes, powders and solids can also be examined utilizing the screen cell by specular and diffuse reflectance where the spectrometer is equipped with the accessory necessary for these determinations. Such accessories are commonly available for UV, VIS, NIR and FTIR spectrometers.

The screen cell can also be utilized to obtain the spectra of microsamples of liquids, paste, powder and solids utilizing the FTIR microscope accessory. Since there are many types of these microscopes, the screen holder must be tailored to the particular accessary.

I claim:

1. An analytic specimen support for infrared microspectroscopy comprising a pair of opposed generally flat surfaces composed of rigid material that is non-reactive to water, acidic substances and solvents and having a plurality of unobstructed holes in a screen disposed between said pair of opposed, generally flat surfaces, the cross-sectional area of each hole being sufficient to retain liquid spanning said hole, the liquid being held in said hole by the surface tension of the liquid and said screen being fitted with a substantially flat plate of absorbent material disposed between said screen and one of said pair of opposed flat surfaces.

2. The support of claim 1 wherein the cross-sectional area of each of said holes is in the range of 0.9 to 1.1 $mm^2$ and adapted to retain about 0.1 microliter of liquid.

* * * * *